United States Patent [19]

Nakashima et al.

[11] 4,421,684

[45] Dec. 20, 1983

[54] COLUMN FOR ADSORPTION OF BLOOD PROTEINS

[75] Inventors: Toshihide Nakashima; Maso Tanihara, both of Kurashiki; Koichi Takakura, Okayama, all of Japan

[73] Assignee: Kuraray Co., Ltd., Kurashiki, Japan

[21] Appl. No.: 383,137

[22] Filed: May 28, 1982

Related U.S. Application Data

[62] Division of Ser. No. 250,630, Apr. 3, 1981, Pat. No. 4,384,954.

[30] Foreign Application Priority Data

Apr. 16, 1980 [JP] Japan .................................. 55-50733
Apr. 16, 1980 [JP] Japan .................................. 55-50734
Sep. 22, 1980 [JP] Japan ................................. 55-131804
Sep. 22, 1980 [JP] Japan ................................. 55-131805
Oct. 29, 1980 [JP] Japan ................................. 55-152457

[51] Int. Cl.$^3$ ....................... A61K 37/02; C07G 7/00
[52] U.S. Cl. ............................. 260/112 B; 210/679; 210/691; 210/927
[58] Field of Search ............... 210/263, 287, 502, 679, 210/691, 692, 927, 690; 252/428, 430, 432, 449, 455 R, 463; 260/112 B

[56] References Cited

U.S. PATENT DOCUMENTS

| 3,637,489 | 1/1972 | Haller | 210/927 |
|---|---|---|---|
| 4,029,583 | 6/1977 | Ho Chang | 210/502 |
| 4,118,316 | 10/1973 | Talley | 210/502 |
| 4,140,653 | 2/1979 | Imura | 210/502 |
| 4,171,283 | 10/1979 | Nakashima | 210/502 |
| 4,199,449 | 4/1980 | Slejko | 210/502 |
| 4,202,775 | 5/1980 | Abe | 210/527 |
| 4,246,351 | 1/1981 | Miyake | 260/112 B |
| 4,248,736 | 2/1981 | Fuchigami | 210/502 |
| 4,284,553 | 8/1981 | Brown | 260/112 B |

Primary Examiner—Ernest G. Therkorn
Attorney, Agent, or Firm—Barry Kramer

[57] ABSTRACT

A column for adsorption of blood proteins is disclosed which comprises a blood inlet and a blood outlet each with a filter, and a porous material packed between both the filters, which material has a mean pore diameter (D) of 30–3,000 amgstroms with the volume occupied by pores with diameters of 0.8D–1.2D being at least 80% of the whole pore volume. The adsorption column can eliminate specific blood proteins by selective adsorption and is useful in the treatment of autoimmune diseases and cancer, for instance.

12 Claims, 3 Drawing Figures

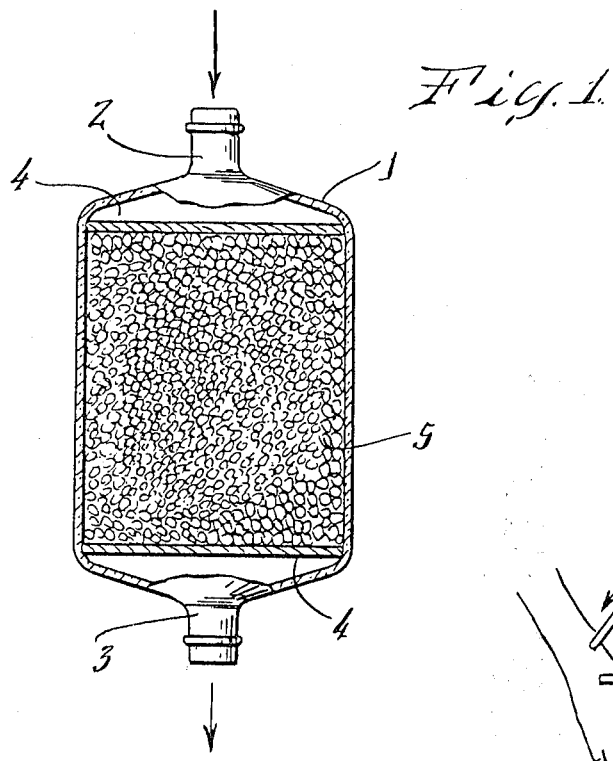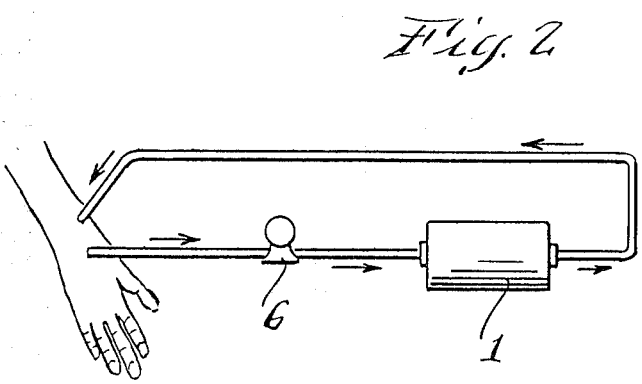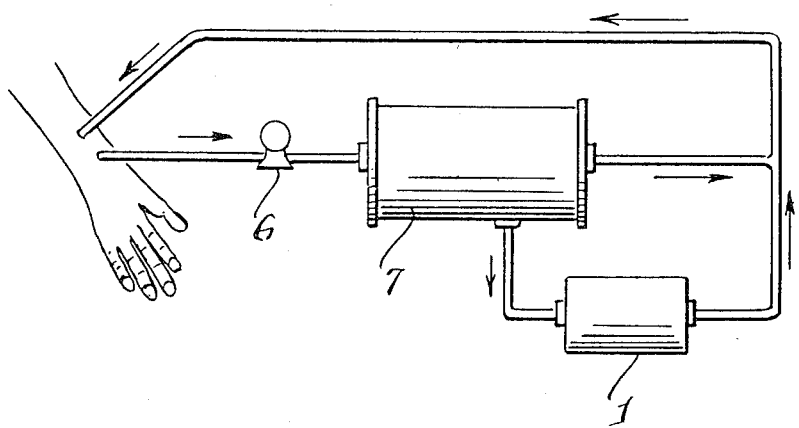

COLUMN FOR ADSORPTION OF BLOOD PROTEINS

This is a division of application Ser. No. 250,630 filed on Apr. 3, 1981, now U.S. Pat. No. 4,384,954.

BACKGROUND OF THE INVENTION

1. Field of the Invention

This invention relates to a column for adsorption of blood proteins and a method of removing blood proteins by adsorption.

2. Description of the Prior Art

Recently, much attention has been drawn to plasma exchange therapy which can produce a significant effect in the treatment of cancer, autoimmune diseases and hepatic insufficiency, for instance. Supposedly, this therapy can remove such proteins as antibodies, immunosuppressive factors and albumin-bound metabolites. However, in the plasma exchange therapy, the plasma of patients is discarded and the plasma of healthy donors is supplied in exchange thereof, consequently several liters of plasma is required each time, and therefore treatment of a large number of patients is difficult. Moreover, useful components are also removed simultaneously with unnecessary protein components, which makes the therapy very wasteful.

On the other hand, blood purification therapy using an adsorbent is advantageous in that unnecessary components alone are removed, hence no or only a small amount of substitute fluid is required. However, when activated carbon or porous resins such as disclosed in Japanese Patent Application Kokai (laid open) Nos. 22,178/1978 (U.S. Pat. No. 4,171,289), 76,219/1975 (GB No. 1,465,519) and 148,291/1976 are used in the treatment of the above diseases, satisfactory therapeutic results can hardly be obtained, because in the case of activated carbon proteins are scarcely adsorbed in spite of adsorption of low-molecular-weight substances such as creatinine and uric acid and, in the case of porous resins useful proteins, vitamins and sugars are simultaneously adsorbed in large quantities together with target proteins.

Such organic polymer adsorbents as disclosed in Japanese Patent Application Kokai Nos. 80,381/1978, 9,183/1979 and 131,586/1979 also have similar disadvantages and are not suited for the object of the present invention.

SUMMARY OF THE INVENTION

An object of the invention is to provide a column for selectively adsorbing specific blood proteins. Another object is to provide a column useful in the treatment of autoimmune diseases, cancerous diseases, hepatic insufficiency, etc., by blood purification. A further object is to provide a method of treating blood wherein specific blood proteins are selectively adsorbed.

BRIEF DESCRIPTION OF THE DRAWINGS

FIG. 1 is a perspective view of an adsorption column of the present invention.

FIG. 2 is a schematic view of a system for adsorbing blood proteins.

FIG. 3 is a schematic view of an another system for adsorbing blood proteins.

DETAILED DESCRIPTION OF THE INVENTION

The adsorption column of the present invention has a blood inlet port and a blood outlet port, each being provided with a filter. The inlet and outlet ports each may be of any structure which enables connection thereof to a blood circuit. The filter is for retaining the packed adsorbent and therefore is required to be of finer mesh or texture as compared with the adsorbent. On the other hand, the filter is also required to allow easy passage of blood therethrough. For treatment of whole blood, it is required that blood corpuscles can easily pass through the filter. For these reasons, it is generally preferable that the filter is of 50–200 mesh. Since the column is used generally after steam autoclaving, the filter should preferably be resistant to steam autoclaving. From this viewpoint, it is preferred that the filter is made of cellulose or, much more preferably, a polyester. The column tube is usually made of a synthetic resin, preferably polypropylene or a polycarbonate. The shape of the column tube should preferably be such that the inside surface is as smooth and even as possible so that smooth passage of blood through the column can be secured.

The adsorbent to be used in this invention is a porous material having a mean pore diameter (D) of 30–3,000 angstroms, with the ratio of the volume occupied by pores with diameters within the range of 0.8D–1.2D to the whole pore volume being at least 80%. When the mean pore diameter is smaller than 30 angstroms, proteins are scarcely adsorbed, whereas, with a mean pore diameter of more than 3,000 angstroms, the porous material will be unsuitably fragile. The porous material to be used in this invention is required to have a narrow or sharp pore size distribution such that, when the mean pore diameter is expresses as D, pores with diameters within the range of 0.8D–1.2D occupy at least 80% of the whole pore volume. When the pore size distribution is wider, the selectivity in adsorption unfavorably becomes decreased; various proteins are adsorbed simultaneously and it is difficult for specific proteins alone to be selectively adsorbed. None of presently available activated carbon or porous organic resins have such a narrow pore size distribution, hence none of them are covered by the present invention.

In the practice of the invention, it is necessary to select the mean pore diameter of the porous material depending on the molecular weight of the protein to be adsorbed. For adsorption of proteins having molecular weights of 5,000 to 20,000, for instance, the use of a porous material having a mean pore diameter within the range of 30–150 angstroms will result in most selective adsorption of proteins having molecular weights within the above-mentioned range. For adsorption of proteins with molecular weights of 20,000–200,000, a mean pore diameter of 150–1,000 angstroms is preferred, whereas, for proteins having molecular weights of 200,000–1,000,000, a mean pore diameter of 1,000–3,000 angstroms is preferred.

The protein which can removed by adsorption in accordance with this invention includes: proteins having molecular weights of 5,000–20,000 such as toxic proteins secreted by poisonous snake, scorpion, poisonous sea urchin, poisonous spider, etc., lysozymes, cytochrome C, and an immunosuppressive factor called "immunoregulatory α-globulin (IRA)" which is found specifically in the blood of cancer patients; proteins having molecular weights of 20,000-200,000 such as γ-globulin, albumin, $\alpha_1$-antitrypsin ($\alpha_1$AT), C-reactive protein (CRP), $\alpha_1$-acid glycoprotein (AAG), immunosuppressive acid protein (IAP), α-fetoprotein (AFP) and other proteinous immunosuppressive factors. γ-Globulin is a group of proteins with molecular weights of about 160,000. Among these proteins, immunoglobulins are causative factors of autoimmune diseases. These factors have to be removed from the blood for treatment of the diseases. Porous materials having mean pore diameters of 350-900 angstroms can adsorb γ-globulins efficiently and selectively. Therefore, in case γ-globulins are to be removed, the use of porous materials having mean pore diameters within the above-mentioned range is especially preferred. The above-mentioned proteinous immunosuppressive factors are found in the blood of cancer patients and have a suppressive activity against the attack of the immune system on cancer cells.

The proteins with molecular weights of 200,000-1,000,000 which can be removed are, for example, complements (e.g. Clq), fibrinogen, microfibrin, and antigen-antibody complexes (immune complexes).

The porous material to be used in this invention includes porous glass, porous silica, porous alumina and porous ceramics. Porous glass can be produced by acid treatment of melt-molded alkali borosilicate glass in which fine phase separation has proceeded as a result of heat treatment at temperatures within the transition temperature region. Porous silica can be produced by acid treatment of an aqueous solution of sodium silicate. Porous alumina can be produced by burning moldings of hydrated alumina, and porous ceramics by sintering a ceramic aggregate with a glass binder. These porous materials are of course required, as mentioned hereinbefore, to have a mean pore diameter (D) of 30-3,000 angstroms and a ratio of the volume occupied by pores with diameters within the range of 0.8D-1.2D of the whole pore volume of 80% or more. Among the above-mentioned porous materials, those having silanol groups on the surface thereof are preferred because they have high protein adsorption capacities but scarcely adsorb useful components such as sugars and vitamins. Therefore, porous glass and porous silica are preferred among the above-mentioned materials, and porous glass is especially preferred because of its high adsorption capacity and great mechanical strength. It is preferable that the porous material has a specific pore volume of not less than 0.1 cc/g, more preferably not less than 0.5 cc/g, and not more than 2 cc/g. Because the porous material having a specific pore volume of less than 0.1 cc/g has low protein adsorption capacity, and the porous material having a specific pore volume of more than 2 cc/g has low mechanical strength. It is preferable that the porous material has a particle size of 4-270 mesh, more preferably 4-50 mesh for adsorption of whole blood proteins and 4-270 mesh for adsorption of plasma or serum proteins.

Although the porous material to be used in this invention may be used as it is, the one coated with a hydrophilic polymer is preferred because of good blood compatibility, that is to say, preventing adhesion of platelet and hemolysis of red blood cell and suppressing activation of complements. The hydrophilic polymer includes polymers based on acrylic acid esters, polymers based on methacrylic acid esters, polymers based on acrylamide, polymers based on vinyl alcohol, polyvinylpyrrolidone, cellulose nitrate and gelatin. Preferred among these are polymers based on acrylic acid esters and polymers based on methacrylic acid esters. More preferable are copolymers of at least one acrylic or methacrylic acid ester of the following general formula (I) or (II) with an epoxy group-containing polymerizable monomer of the general formula (III), (IV) or (V):

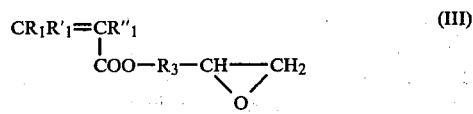

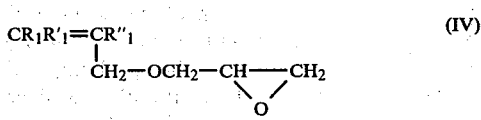

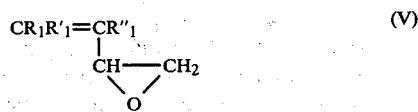

wherein, in the formulas, $R_1$, $R_1'$ and $R_1''$ are each H or methyl; $R_2$ is a bivalent alkylene group containing 2-3 carbon atoms which may have a substituent or substituents, or a poly(oxyalkylene) group; $R_3$ is a bivalent alkylene group containing 1-3 carbon atoms which may be substituted, or a poly(oxyalkylene) group; $R_4$ and $R_4'$ are each H or an alkyl group containing 1-3 carbon atoms which may have a hydroxyl or amino group.

The porous material coated with such a hydrophilic polymer should be sterilized, preferably by autoclaving, prior to use thereof for therapeutic purposes. For preventing the polymer from dissolution from the coat layer during sterilization, it is recommended that a copolymer containing as a constituent unit an epoxy group-containing polymerizable monomer represented by the above general formula (III), (IV) or (V) be used as a coating agent and subsequently be cured or cross-linked e.g. by heat treatment to make the same water-insoluble. The suitable content of the epoxy group-containing polymerizable monomer is 0.1-10% by weight.

The porous material can be coated with the hydrophilic polymer by applying a solution of said polymer in an adequate solvent such as methanol or ethanol to the porous material by immersion or spraying or by the wet coagulation method. The coat layer is required to be the one which can add an adequate degree of blood compatibility to the porous material without significantly lowering the adsorption capacity of the porous material. From this viewpoint, the suitable concentration of the hydrophilic polymer in the solution thereof to be used in the coating treatment is in the range of 0.05-2%, more preferably 0.05-0.5%.

When the porous material is coated with a copolymer containing as a constituent unit an epoxy group-containing monomer represented by the above general formula (III), (IV) or (V), crosslinking can be effected by heating at 80°-120° C. for 1-24 hours to render the copolymer water-insoluble.

The porous material to be used in this invention can further be improved in the selectivity of adsorption by introducing an electric charge onto the surface thereof. When the proteins to be adsorbed are basic proteins, negatively charged groups such as carboxyl or sulfo are introduced, and, for acidic proteins, positively charged groups such as amino are introduced. For example, the amino group introduction can be carried out by treating the porous material with an aminosilane compound such as γ-aminopropyltriethoxysilane, and the carboxyl group introduction can be effected by reacting the aminosilanated porous material with succinic anhydride or with succinic acid in the presence of a carbodiimide. The sulfo group introduction can be realized, for example, by introducing an aldehyde group by treatment with glutaraldehyde in acidic conditions following the aminosilanation and then treating the intermediate product with taurine in alkaline conditions. Another charge introduction method comprises coating the porous material with a carboxyl, sulfo or amino group-containing polymer. Examples of such polymer are polyacrylic acid, polymethacrylic acid, polystyrenesulfonic acid and copolymers of monomers which are constituent units of said polymers with hydrophilic monomers. The suitable concentration of the carboxyl, sulfo or amino group-containing polymer in the solution thereof to be used in the coating treatment is in the range of 0.05–5.0%, more preferably 0.1–2%.

For adsorption of albumin which is anacidic protein, for instance, the use of porous materials with amino groups introduced on the surface thereof will result in highly selective adsorption of albumin.

As previously mentioned, the porous material to be used in this invention is required to have a mean pore diameter and a pore size distribution each falling within the above-specified range. The mean pore diameter and pore size distribution values are those as measured with a mercury porosimeter.

Having a narrow pore size distribution, the porous material in accordance with this invention is excellent in the selectivity in protein adsorption. By using a porous material having a specific mean pore diameter selected according to the molecular weight of the protein to be adsorbed, the undesirable protein can be adsorbed efficiently without substantial adsorption of useful blood components. As mentioned previously, the relationship between the molecular weight of the protein and the mean pore diameter is such that mean pore diameters of 30–150 angstroms, 150–1,000 angstroms and 1,000–3,000 angstroms are for molecular weights of 5,000–20,000, 20,000–200,000 and 200,000–1,000,000, respectively.

On the contrary, activated carbon and porous resins so far used in the art in removing harmful components in the blood by adsorption are unpreferable because they adsorb not only the target proteins but also useful proteins, sugars and vitamins due to their pore size distribution being much wider.

Referring to the accompanying drawing, the column for blood protein adsorption in accordance with the present invention is described in more detail. FIG. 1 shows an example of the adsorption column of this invention. The main body 1 has a blood inlet port 2 and a blood outlet port 3. The inlet and outlet ports are each provided with a filter 4. Between the filters, there is packed a porous material 5 which features the present invention. Blood enters inlet 2, passed through filter 4, comes into contact with porous material 5, whereby proteins are adsorbed on the porous material, and leaves the column through outlet 3.

For removal of blood proteins by adsorption using the adsorption column of this invention, in accordance with the embodiment shown in FIG. 2, the blood is taken out of a patient, fed to the adsorption column by means of a pump 6, and, after removal of proteins by adsorption, returned to the patient. In addition to such a generally utilizable system, there is another system wherein, as shown in FIG. 3, the blood is taken out of a patient and subjected to separation into a blood corpuscular fraction and a plasma fraction by means of a plasma separator 7, the plasma fraction alone is passed through adsorption column 1 for protein removal by adsorption and then combined with the corpuscular fraction and the mixture is returned to the patient. An optimal system can be selected from these arbitrarily depending on the objective. The column can also be built into a system other than these extracorporeal circulation systems.

As stated hereinbefore, the present invention makes it possible to treat various diseases, since specific proteins present in blood can now be removed selectively by adsorption thereof. The blood described in the present invention includes whole blood, plasma and serum. For example, in autoimmune diseases (such as autoimmune hemolytic anemia, glomerulonephritis, chronic rheumatoid arthritis, systemic lupus erythematosus, systemic scleroderma, nodal periarteritis and etc.), antibodies (immunoglobulins with molecular weights of about 160,000) against the patient's own organs or body components are produced and these are main causative factors. The antibodies are present in blood per se or in the form of antigen-antibody complexes (immune complexes, having molecular weights of 200,000–1,000,000). Therefore, therapeutic treatment can be effected by removing immunoglobulins by adsorption using a porous material having a mean pore diameter of 350–900 angstroms, or by removing antigen-antibody complexes by adsorption using a porous material having a mean pore diameter of 1,000–3,000 angstroms. Also in organ transplantation where antibodies (immunoglobulins) are formed against the organs transplanted and cause rejection reaction, the rejection reaction can be overcome by removing the antibodies by adsorption using the above-mentioned porous material. Furthermore, in the blood of patients with cancer, there are present immunosuppressive factors which are supposed to be antigens, such as immunoregularoty α-globulin (IRA, mol. wt.: 500–10,000), $\alpha_1$-antitrypsin ($\alpha_1$AT), C-reactive protein (CRP, mol. wt.: about 140,000), $\alpha_1$-acid glycoprotein (AAG), immunosuppressive acid protein (IAP, mol. wt.: about 59,000) and α-fetoprotein (AFP, mol. wt.: about 74,000), as well as immunosuppressive factors which are supposed to be antibodies (mol. wt.: 100,000–200,000), and the attack of the immune system on cancer cells is avoided thereby. Since the amounts of these immunosuppressive factors are different according to the kind of cancer, the cancer can be treated by removing the main immunosuppressive factors by adsorption using a porous material having an adequate mean pore diameter (30–150 angstroms for IRA; 150–1,000 angstroms for others).

In the case of hepatic inssufficiency, a large amount of metabolites (e.g. bilirubin) is present in blood in the form of the albumin-bound form and causes jaundice. Therefore, this can be treated by removing the albumin-bound metabolites using a porous material having a mean pore diameter of 150–1,000 angstroms and an amino group on the surface.

As stated hereinbefore, the present invention is useful in the treatment of various diseases. When necessary, a column with two or more porous materials packed therein or a plurality of columns may be used, for increasing the therapeutic effect or for treating two or more diseases at a time.

Generally, the column of the invention is used after sterilization. Preferred sterilization methods are, among others, steam sterilization under pressure and γ-ray sterilization.

The following examples further illustrate the present invention.

EXAMPLE 1

Porous glass CPG-10-75 (mean pore diameter D=90 angstroms, ratio of the volume occupied by pores with diameters of 0.8D-1.2D to the whole pore volume=98%, specific pore volume=0.54 cc/g, surface area=174 m²/g, particle size=80-120 mesh) (Example 1-1), a product of Electro Nucleonics, Inc., was treated with γ-aminopropyltriethoxysilane in refluxing toluene for amino group introduction and then reacted with succinic anhydride in anhydrous dioxane to give carboxylated porous glass (Example 1-2). Separately, porous glass CPG-10-75 was immersed in a 1% (by weight) solution of a copolymer consisting of 79% hydroxyethyl methacrylate, 20% methacrylic acid and 1% glycidyl methacrylate in ethanol, then dried and heated to give porous glass coated with the carboxyl group-containing hydrophilic polymer (Example 1-3).

Porous glass FPG-100L (mean pore diameter D=96 angstroms, ratio of the volume occupied by pores with diameters of 0.8D-1.2D to the whole pore volume=82%, specific pore volume=0.60 cc/g, surface area=171 m²/g, particle size=80-120 mesh) (Example 1-4), a product of Wako Pure Chemical Industries, Ltd., was carboxylated in the same manner as in Example 1-2 to give a product (Example 1-5). Porous glass FPG-100L was coated with the same hydrophilic polymer in the same manner as in Example 1-3 to give a product (Example 1-6).

Furthermore, porous glass CPG-10-170 (mean pore diameter D=220 angstroms, ratio of the volume occupied by pores with diameters to the whole pore volume=90%, specific pore volume=1.23 cc/g, surface area=140 m²/g, particle size=80-120 mesh) (Example 1-7) and porous glass CPG-10-240 (mean pore diameter D=370 angstroms, ratio of the volume occupied by pores with diameters of 0.8D-1.2D to the whole pore volume=86%, specific pore volume=1.34 cc/g, surface area=97 m²/g, particle size=80-120 mesh) (Example 1-8), each a product of Electro Nucleonics, Inc., were used. Activated bead carbon BAC-MU-L (a product of Kureha Chem. Ind. Co., having broad pore size distribution) was used as a control Example (Example 1-9).

These materials were tested for their capacities for adsorbing egg white lysozyme (Sigma), equine heart cytochrome C (Sigma) and bovine serum albumin (Fraction V, Sigma). The results obtained are shown in Table 1.

TABLE 1

Protein Adsorption Capacities (in 3 hours)*

| Example No. (Porous glass) | Mean pore diameter | Lysozyme (mol. wt. 14,600) | Cytochrome C (mol. wt. 12,800) | Albumin (mol. wt. ca. 60,000) |
|---|---|---|---|---|
| 1-1 (CPG-10-75) | 90 Å | 111.0 mg/g | — mg/g) | 0 mg/g |
| 1-2 (CPG-10-75) | 90 | 61.2 | — | 0 |
| 1-3 (CPG-10-75) | 90 | 69.2 | 55.8 | 0 |
| 1-4 (FPG-100L) | 96 | 90.6 | — | 0 |
| 1-5 (FPG-100L) | 96 | 80.4 | — 0 | |
| 1-6 (FPG-100L) | 96 | 67.8 | 102.6 | 0 |
| 1-7 (CPG-10-170) | 220 | 112.8 | 114.0 | 67.8 |
| 1-8 (CPG-10-240) | 370 | 106.0 | — | 59.0 |
| 1-9 (control) (BAC-MU-L) | | 7.8 | — | 2.4 |

*Calculated from the supernatant protein concentration. They were assayed for albumin by the bromocresol green method and for cytochrome C by UV adsorption and for lysozyme by the biuret method.
Test conditions: Initial protein concentration: lysozyme 2 g/dl, albumin 2 g/dl, cytochrome C 2 g/dl, in 0.9% phosphate-buffered saline; bath ratio: 3 ml/0.5 g of adsorbent; 37° C., with shaking at 120 cycles per minute (cpm).

As is evident in Table 1, the porous materials of Example 1-1 to Example 1-6 each having a mean pore diameter smaller than 150 angstroms well adsorbed the lysozyme and cytochrome C, which are low-molecular-weight proteins, but did not adsorb the serum albumin at all. On the contrary, the porous materials of Example 1-7 and Example 1-8 each having a mean pore diameter greater than 150 angstroms were low in the selectivity for either the lysozyme or serum albumin.

EXAMPLE 2

Porous glass CPG-10-240 (see Example 1-8) (Example 2-1), a product of Electro Nucleonics, Inc., was immersed in a 1% (by weight) solution of a copolymer composed of 79 weight % hydroxyethyl methacrylate, 20 weight % methacrylic acid and 1 weight % glycidyl methacrylate in ethanol, then dried and heated to give porous glass coated with the hydrophilic polymer (Example 2-2).

Porous glass FPG-250L (mean pore diameter D=220 angstroms, ratio of the volume occupied by pores with diameters of 0.8D-1.2D to the whole pore volume=96%, specific pore volume=0.89 cc/g, surface area=103 m²/g, particle size=80-120 mesh) (Example 2-3), a product of Wako Pure Chemical Industries, Ltd., was coated with the same hydrophilic polymer in the same manner as in Example 2-2 to give a product (Example 2-4).

Porous glass FPG-100L (see Example 1-4) (Example 2-5), Wako's product, was coated with the same hydrophilic polymer in the same manner as in Example 2-2 to give a product (Example 2-6). Activated bead carbon BAC-MU-L (see Example 1-9) was used as a control Example (Example 2-7).

The adsorption capacities of these materials for bovine serum albumin (Fraction V, Sigma) and bovine serum γ-globulin (Fraction II, Sigma) were as shown in Table 2.

As is evident in the table, the porous materials of Example 2-1 to Example 2-4 each having a mean pore diameter greater than 150 angstroms well adsorbed the albumin and gammaglobulin, but the porous materials of Example 2-5 and Example 2-6 having a mean pore diameter smaller than 150 angstroms did not adsorb the albumin and γ-globulin at all.

TABLE 2

| | Protein Adsorption Capacities (in 3 hours)* | | |
|---|---|---|---|
| Example No. | Mean pore diameter | Bovine serum albumin (mol. wt. ca. 60,000) | Bovine serum γ-globulin (mol. wt. ca. 160,000) |
| 2-1 | 370 Å | 60 mg/g | 53 mg/g |
| 2-2 | " | 44 | 28 |
| 2-3 | 220 | 83 | 36 |
| 2-4 | " | 70 | 20 |
| 2-5 | 96 | 0 | 0 |
| 2-6 | " | 0 | 0 |
| 2-7 | | 2.4 | 0 |

*Calculated from the protein concentration in the supernatant. They were assayed for albumin by the bromocresol green method and for total protein by the biuret method, and the γ-globulin concentration was calculated as the difference between the total protein and albumin.
Test conditions: Initial protein concentration: bovine serum albumin 2 g/dl, bovine serum γ-globulin 2 g/dl, mixed in phosphate-buffered saline; bath ratio; 6 ml/g of adsorbent; 37° C., with shaking at 120 cpm.

EXAMPLE 3

0.5 g each of porous glass CPG-10-240 (see Example 1-8) (Example 3-1), CPG-10-500 (mean pore diameter D=700 angstroms, ratio of the volume occupied by pores with diameters of 0.8D-1.2D to the whole pore volume=99%, specific pore volume=0.87 cc/g, surface area=39 m²/g, particle size=80-120 mesh) (Example 3-2) and CPG-10-700 (mean pore diameter D=880 angstroms, ratio of the volume occupied by pores with diameters of 0.8D-1.2D to the whole pore volume=99%, specific pore volume=1.25 cc/g, surface area 37 m²/g, particle size=80-120 mesh (Example 3-3), each a product of Electro Nuclenoics, Inc., was taken, 3 ml of a solution of bovine serum albumin (Fraction V, Sigma) and bovine serum γ-globulin (Fraction II, Sigma) in a phosphate-buffered saline solution with a concentration of each protein of 2 g/dl was added, and the mixture was shaken at B 37° C. at a rate of 120 cycles per minute. The supernatant was sampled at intervals and assayed for albumin by the bromocresol green method and for total protein by the biuret method, and the γ-globulin concentration was calculated as the difference between the total protein and albumin. The mean pore diameters of the porous glass species used and the adsorption capacities thereof for the albumin and γ-globulin were as shown in Table 3. When compared with the results obtained in Example 2, these results indicate that the porous materials having mean pore diameters of 350-900 angstroms are excellent in the adsorption selectivity for γ-globulin.

TABLE 3

| | Protein Adsorption Capacities (in 3 hours) | | |
|---|---|---|---|
| Example No. | Mean pore diameter | γ-Globulin | Albumin |
| 3-1 | 370 Å | 53.1 mg/g | 58.2 mg/g |
| 3-2 | 700 | 34.8 | 25.2 |
| 3-3 | 880 | 42.6 | 36.6 |

EXAMPLE 4

25 Grams each of porous glass CPG-10-500 (see Example 3-2), CPG-10-700 (see Example 3-3) and CPG-10-1000 (mean pore diameter D=1,300 angstroms, ratio of the volume occupied by pores with diameters of 0.8D-1.2D to the whole pore volume=90%, specific pore volume=1.05 cc/g, surface area=28 m²/g, particle size=80-120 mesh), a product of Electro Nucleonics, Inc., was immersed in 200 ml of a 5% γ-aminopropyltriethoxysilane solution in toluene and heated under reflux overnight. The thus aminated CPG's were washed with toluene and dried. 10 g of each aminated CPG was immersed in 100 ml of a 10% succinic anhydride solution in dioxane, and the mixture was shaken at 40° C. for 7 hours. The thus carboxylated CPG's (which are Example 4-1, 4-2, 4-3, respectively) were washed with dioxane and dried. 0.5 g of each carboxylated CPG was taken and tested for the adsorption capacities for albumin and γ-globulin by the same methods as used in Example 3. The results obtained are shown in Table 4.

TABLE 4

| | Protein Adsorption Capacities of Carboxylated CPG's (in 3 hours) | | |
|---|---|---|---|
| Example No. | Mean pore diameter | γ-Globulin | Albumin |
| 4-1 | 700 Å | 36.0 mg/g | 31.2 mg/g |
| 4-2 | 880 | 68.9 | ~0 |
| 4-3 | 1,300 | 27.6 | 27.6 |

EXAMPLE 5

The carboxylated CPG-10-1000 with a mean pore diameter of 1,300 angstroms prepared in Example 4 was coated with a hydroxyethyl methacrylate-methacrylic acid copolymer by spray method, the weight percent of the coat layer being 0.2%. The product was tested for the adsorption capacities for albumin and γ-globulin by the same methods as used in Example 3. The adsorption capacities for albumin and γ-globulin in 3 hours were 15.0 mg/g and 75.0 mg/g, respectively. It was thus revealed that this coating treatment decreases the albumin adsorption capacity of the carboxylated CPG but increases the γ-globulin adsorption capacity thereof.

EXAMPLE 6

Porous glass CPG-10-1000 (see Example 4), a product of Electro Nuclenonics, Inc., was coated with polyacrylic acid by spray method (the weight percent of the coat being 0.5%), and then heated at 120° C. for 2 hours. The product was tested for the adsorption capacities for albumin and γ-globulin by the same methods as used in Example 3. The adsorption capacities for albumin and γ-globulin in 3 hours were 42.0 mg/g and 60.0 mg/g, respectively. It was thus shown that also coating with a carboxyl-containing polymer results in an increase in the γ-globulin adsorption capacity of the CPG.

EXAMPLE 7

Porous glass CPG-10-500 (see Example 3-2), a product of Electro Nucleonics, Inc., was aminosilanated in the same manner as in Example 4. 5 g of the silanation product was taken, 50 ml of a 5% glutaraldehyde solution in 1-N hydrochloric acid was added, and the mixture was shaken at room temperature for 17 hours. The CPG was washed well with water, then 50 ml of a 5% taurine solution in 1-N sodium hydroxide was added, and the mixture was shaken at room temperature for 8 hours. The thus-obtained sulfo-terminated CPG was tested for the adsorption capacities for albumin and γ-globulin by the same methods as used in Example 3. The amounts of albumin and γ-globulin adsorbed in 3 hours were 25.8 mg/g and 63.6 mg/g, respectively. The results indicate that the sulfo group introduction causes a greater increase in the adsorption selectivity for γ-globulin than the carboxyl group introduction.

EXAMPLE 8

25 g each of porous glass species CPG-10-500 (see Example 3-2), CPG-10-700 (see Example 3-3) and CPG-10-1000 (see Example 4), products of Electro Nucleonics, Inc., was immersed in 200 ml of a 5% solution of γ-aminopropyltriethoxysilane in toluene and heated under reflux overnight. 0.5 g each of the untreated CPG's (which are Example 8-1, 8-3, 8-5, respectively) and the aminated CPG's (which are Example 8-2, 8-4, 8-6, respectively) was tested for the adsorption capacities for albumin and γ-globulin by the same methods as used in Example 3. The results obtained are shown in Table 5. For any of the mean pore diameters, the results show that the amino group introduction increases the adsorption capacity for albumin but decreases the adsorption capacity for γ-globulin.

TABLE 5

Protein Adsorption Capacities of Porous Glass Species (in 3 hours)

| Example No. | Mean pore diameter | Amino group introduction | Albumin | γ-Globulin |
|---|---|---|---|---|
| 8-1 | 700 Å | Not made | 25.2 mg/g | 34.8 mg/g |
| 8-2 | " | Made | 38.4 | ~0 |
| 8-3 | 880 | Not made | 36.6 | 42.6 |
| 8-4 | " | Made | 53.4 | 3.6 |
| 8-5 | 1,300 | Not made | 48.0 | 9.0 |
| 8-6 | " | Made | 64.2 | ~0 |

EXAMPLE 9

Porous glass CPG-10-1400 (mean pore diameter D=1,400 angstroms, ratio of the volume occupied by pores with diameters of 0.8D–1.2D to the whole pore volume=99%, specific pore volume=0.66 cc/g, surface area=8.3 m²/g, particle size=80-120 mesh), a product of Electro Nucleonics, Inc., was treated in refluxing toluene with γ-aminopropyltriethoxysilane. The amination product was then reacted with succinic anhydride in anhyrous dioxane to give a carboxyl group-carrying CPG-10-1400 modification (Example 9-1).

Porous glass CPG-10-2000 (mean pore diameter D=2,800 angstroms, ratio of the volume occupied by pores with diameters of 0.8D–1.2D to the whole pore volume=99%, specific pore volume=0.66 cc/g, surface area=8.3 m²/g, particle size=80-120 mesh) (Example 9-2), a product of the same company, was treated in the same manner as in Example 9-1 to give a carboxyl group-carrying modification (Example 9-3). Furthermore, porous glass CPG-10-2000 was immersed in a 1% (by weight) solution of a copolymer prepared from 79 weight % of hydroxyethyl methacrylate, 20 weight % of methacrylic acid and 1 weight % of glycidyl methacrylate in ethanol, then dried and heat-treated to give a CPG-10-2000 modification coated with the hydrophilic polymer (Example 9-4).

Porous glass FPG-2000L (mean pore diameter D=2,200 angstroms, ratio of the volume occupied by pores with diameters of 0.8D–1.2D to the whole pore volume=90%, specific pore volume=0.92 cc/g, surface area 14 m²/g, particle size=80-120 mesh) (Example 9-5), a product of Wako Pure Chemical Industries, Ltd., was treated in the same manner as in Example 9-1 to give a surface carboxyl group introduction product (Example 9-6).

Porous glass CPG-10-700 (see Example 3-3) (Example 9-7), a product of Electro Nucleonics, Inc., was treated in the same manner as in Example 9-1 to give a surface carboxyl group introduction product (Example 9-8).

These porous materials were tested for the adsorption capacities for urease (Type III, Sigma, mol. wt.=470,000) and for bovine γ-globulin (Fraction II, Sigma, mo. wt.=160,000). A mixture of each material and a solution of the proteins in phosphate-buffered saline at a bath ratio of 6 ml/g of adsorbent was shaken at 37° C. for 3 hours, the initial concentration of each protein being 2 g/dl. The protein concentrations in the supernatant were determined by the biuret method, and the adsorption capacities for the proteins were calculated therefrom. The results obtained are shown in Table 6.

TABLE 6

Protein Adsorption Capacities (in 3 hours)

| Example No. | Mean pore diameter | Urease | γ-Globulin |
|---|---|---|---|
| 9-1 | 1,400 Å | 9.6 mg/g | 3.0 mg/g |
| 9-2 | 2,800 | 5.4 | — |
| 9-3 | 2,800 | 18.6 | 0 |
| 9-4 | 2,800 | 12.0 | 0 |
| 9-5 | 2,200 | 2.0 | 0 |
| 9-6 | 2,200 | 16.2 | 1.2 |
| 9-7 | 880 | 3.5 | 45.0 |
| 9-8 | 880 | 2.0 | 69.0 |

As is clear from the data in Table 6, the use of the porous materials each having a mean pore diameter within the range of 1,000–3,000 angstroms in Example 9-1 to Example 9-6 results in selective adsorption of urease, which is a high-molecular-weight protein, but almost no adsorption of the low-molecular-weight γ-globulin. On the contrary, the porous materials with a mean pore diameter smaller than 1,000 angstroms used in Example 9-7 and Example 9-8 adsorb almost no urease but adsorb γ-globulin in relatively large amounts.

EXAMPLE 10

Porous material CPG-10-1400 (see Example 9), a product of Electro Nucleonics, Inc., was used in Example 10-1. Porous glass FPG-700L (mean pore diameter D=720 angstroms, ratio of the volume occupied by pores with diameters of 0.8D–1.2D to the whole pore volume=99%, specific pore volume=0.95 cc/g, surface area=37 m²/g, particle size=80-120 mesh), a product of Wako Pure Chemical Industries, Ltd., was treated in the same manner as in Example 9-1 for surface carboxyl group introduction, and the product was used in Example 10-2. The adsorption capacities for bovine liver catalase (Miles Laboratories, mol. wt.=240,000) under the same test conditions as in Example 9-1 to Example 9-6 except that the initial protein concentration was 2.3 g/dl. The results obtained are shown in Table 7. The data show that a porous material having a mean pore diameter of not less than 1,000 angstroms is required for adsorption of catalase with a molecular weight of 240,000.

TABLE 7

Protein (Catalase) Adsorption Capacities (in 3 hours)

| | Mean pore diameter | Catalase |
|---|---|---|
| Example 10-1 | 1,400 Å | 19.0 mg/g |

TABLE 7-continued

| Protein (Catalase) Adsorption Capacities (in 3 hours) | | |
| --- | --- | --- |
| | Mean pore diameter | Catalase |
| Example 10-2 | 720 | 0 |

EXAMPLE 11

50 ml of CPG-10-350 (mean pore diameter D=380 angstroms, ratio of the volume occupied by pores with diameters of 0.8D–1.2D to the whole pore volume=86%, specific pore volume=1.39 cc/g, surface area=90 m²/g, particle size=80–120 mesh), a product of Electro Nucleonics, Inc., which was immersed in a 0.25% (by weight) solution of a copolymer consisting of 99.5% hydroxymethyl methacrylate and 0.5% glycidyl methacrylate in ethanol, then dried and heated, was packed in a polypropyrene column (both ends of which were fitted with a 180 mesh polyester filter). Whole blood of a rabbit (3.46 kg, ♂) was circulated in the column in vivo for one hour at the flow rate about 5 ml/min. Aliquots of the blood were taken from the arterial line and the venous line, and the plasma were obtained by centrifugation. The plasma were analyzed with a High Performance Liquid Chromatography (apparatus: ALC/GPC Type 244 (Waters Associates Inc.), column: G-3000SW (ID 7.5 mm, L 600 mm, Toyo Soda), eluent: 1/15 M phospate buffer (0.15 M NaCl, pH 6.0), flow rate: 1.0 ml/min, detector: UV (280 nm), and from the obtained peak heights of the chromatogram the removal rates of albumin and γ-globulin were calculated, respectively.

The results shown in Table 8 obviously indicate that 70% of γ-globulin in blood was removed within 1 hours, but albumin was decreased only 20%.

TABLE 8

| Removal of Albumin and γ-Globulin in the Rabbit Blood | | |
| --- | --- | --- |
| Circulating time | Albumin (%) | γ-Globulin (%) |
| 1 hour | Arterial 23 | 63 |
| | Venous 27 | 68 |

EXAMPLE 12

2 Grams of CPG-10-75 (see Example 1) was packed in a polypropyrene column (see Example 11), and in which 15 ml of a rabbit whole blood containing 120 mg of egg white lysozyme was circulated at 37° C. for three hours at the flow rate about 3 ml/min. Concentrations of lysozyme, albumin and γ-globulin in each time were determined by the same method as shown in Example 11.

From the results in Table 9, it is clearly shown that lysozyme was specifically removed within three hours in contrast with that albumin and γ-globulin were not removed at all.

TABLE 9

| Removal of Lysozyme in Rabbit Blood | | | |
| --- | --- | --- | --- |
| Circulating time | Lysozyme (%) | Albumin (%) | γ-Globulin (%) |
| 1 hour | 95 | 0 | 0 |
| 2 hour | 99 | 0 | 0 |
| 3 hour | 100 | 0 | 0 |

EXAMPLE 13

Rabbit anti-bovine serum albumin antiserium obtained from the rabbit immunized by bovine serum albumin (BSA) was incubated with 100 mg of BSA at 37° C. for thirty minutes. It was filtered by 0.2μ membrane filter, and then obtained the rabbit serum containing soluble immune-complex.

Carboxylated CPG-10-2000 (see Example 9-3) was packed in a polypropyrene column (analogous type column in that of Example 12), and 10 ml of the above mentioned rabbit serum was circulated through this column at 37° C. for three hours at the flow rate about 3 ml/min. The change of the immune-complex concentrations in the rabbit serum was analyzed by HPLC (same condition as shown in Example 11 except that the column was G-4000SW (ID 7.5 mm, L 600 mm, Toyo Soda)).

The results are shown in Table 10. The immune-complex decreased about 30% within three hours, but other proteins which are almost albumin and γ-globulin decreased only 7%. It was obviously proven that the column in this invention was able to remove immune-complex in rabbit serum selectively.

TABLE 10

| Removal of Immune-Complex in Rabbit Serum | | |
| --- | --- | --- |
| Circulating time | Immune-Complex (%) | Other Proteins (%) |
| 1 hour | 5 | 0 |
| 2 hour | 8 | 0 |
| 3 hour | 30 | 7 |

What is claimed is:

1. A method of removing blood proteins by adsorption which comprises bringing blood, plasma or serum into contact with porous glass having a mean pore diameter in the range of 30–3,000 angstroms with the ratio of the volume occupied by pores with diameters within the range of 0.8D–1.2D to the whole pore volume being at least 80%, D being the mean pore diameter, and with the mean pore diameter of the porous glass being selected to correspond to the molecular weights of the proteins to be adsorbed as follows:
  (a) for adsorption of proteins having molecular weights of 500–20,000, porous glass with a mean pore diameter in the range of 30–150 angstroms is used;
  (b) for adsorption of proteins having molecular weights of 20,000–200,000, porous glass with a mean pore diameter in the range of 150–1,000 angstroms is used; and
  (c) for adsorption of proteins having molecular weights of 200,000–1,000,000, porous glass with a mean pore diameter in the range of 1,000–3,000 angstroms is used.

2. A method of removing blood proteins by adsorption as claimed in claim 1, wherein the mean pore diameter of the porous glass is within the range of 350–900 angstroms so that γ-globulin can be adsorbed thereon.

3. A method of removing blood proteins by adsorption as claimed in any one of claims 1 or 2, wherein the porous glass is coated with a hydrophilic polymer.

4. A method of removing blood proteins by adsorption as claimed in claim 3, wherein the hydrophilic polymer is selected from the group consisting of polymers based on acrylic acid esters, polymers based on methacrylic acid esters, polymers based on acrylamide, polymers based on vinyl alcohol, polyvinylpyrrolidone, cellulose nitrate and gelatin.

5. A method of removing blood proteins by adsorption as claimed in claim 3, wherein the hydrophilic polymer is a polymer based on an acrylic or methacrylic acid ester.

6. A method of removing blood proteins by adsorption as claimed in claim 3, wherein the hydrophilic polymer is an acrylic or methacrylic acid-based polymer in which an epoxy group-containing polymerizable monomer is copolymerized.

7. A method of removing blood proteins by adsorption as claimed in any one of claims 1 or 2, wherein the surface of the porous glass is negatively charged.

8. A method of removing blood proteins by adsorption as claimed in any one of claims 1 or 2, wherein the porous glass carries carboxyl or sulfo groups on the surface thereof.

9. A method of removing blood proteins by adsorption as claimed in any one of claims 1 or 2, wherein the porous glass carries silanol groups on the surface thereof.

10. A method of removing blood proteins by adsorption as claimed in any one of claims 1 or 2, wherein the porous glass is produced by acid treatment of alkali borosilicate glass having a fine phase separation structure.

11. A method of removing blood proteins by adsorption as claimed in any one of claims 1 or 2, wherein the specific pore volume of the porous glass is not less than 0.5 cc/g.

12. A method of removing blood proteins by adsorption as claimed in any one of claims 1 or 2, wherein the specific pore volume of the porous glass is within the range of 0.5-2 cc/g.

* * * * *